(12) United States Patent
Cosgriff-Hernandez et al.

(10) Patent No.: US 9,180,094 B2
(45) Date of Patent: Nov. 10, 2015

(54) HIGH POROSITY MATERIALS, SCAFFOLDS, AND METHOD OF MAKING

(71) Applicant: The Texas A&M University System, College Station, TX (US)

(72) Inventors: Elizabeth M. Cosgriff-Hernandez, College Station, TX (US); Robert Scott Moglia, College Station, TX (US); Jennifer L. Robinson, College Station, TX (US); Nicholas A. Sears, College Station, TX (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 399 days.

(21) Appl. No.: 13/651,362

(22) Filed: Oct. 12, 2012

(65) Prior Publication Data
US 2013/0287735 A1    Oct. 31, 2013

Related U.S. Application Data

(60) Provisional application No. 61/546,496, filed on Oct. 12, 2011.

(51) Int. Cl.
*A61L 27/38*      (2006.01)
*A61K 9/107*      (2006.01)
(Continued)

(52) U.S. Cl.
CPC ................ *A61K 9/107* (2013.01); *A61K 9/122* (2013.01); *A61L 27/16* (2013.01); *A61L 27/38* (2013.01); *A61L 27/50* (2013.01); *A61L 27/56* (2013.01); *A61L 2300/802* (2013.01)

(58) Field of Classification Search
CPC ....................................................... A61L 27/38
See application file for complete search history.

(56) References Cited

U.S. PATENT DOCUMENTS

| 5,900,437 A | 5/1999 | Mitchell et al. |
| 6,750,261 B1 | 6/2004 | Clear et al. |

(Continued)

FOREIGN PATENT DOCUMENTS

| CN | 1923298 A | 3/2007 |
| CN | 101066473 A | 11/2007 |

(Continued)

OTHER PUBLICATIONS

Christenson et al (Biomacromolecules 2007, 8, 3806-6814).*

(Continued)

*Primary Examiner* — Benjamin Packard
(74) *Attorney, Agent, or Firm* — Gardere Wynne Sewell LLP

(57) ABSTRACT

Materials and methods for preparing three dimensional scaffolds are described. The materials, as improved high internal phase emulsions (HIPES), and the polymerization thereof may be suitable for injection prior to curing and when in an injectable form may be for site-directed in vivo use, curing after injection. In addition, said materials before curing may be engineered as a tissue substitution or enhancement and/or to include cell encapsulation. Said materials described herein form a monolith after curing and are biodegradable and porous after curing. Said materials are made from starting molecules using a process that does not rely on toxic solvents or monomers. Making of said materials to form the emulsion take advantage of one or more surfactants for HIPE stability. In addition, said materials cure at temperatures appropriate for use in an in vivo or in situ environment.

24 Claims, 11 Drawing Sheets
(8 of 11 Drawing Sheet(s) Filed in Color)

(51) Int. Cl.
| | |
|---|---|
| A61K 9/12 | (2006.01) |
| A61L 27/56 | (2006.01) |
| A61L 27/16 | (2006.01) |
| A61L 27/50 | (2006.01) |

(56) References Cited

U.S. PATENT DOCUMENTS

| | | |
|---|---|---|
| 6,750,263 B2 | 6/2004 | Sasabe et al. |
| 6,759,080 B2 | 7/2004 | Thunhorst et al. |
| 6,765,029 B2 | 7/2004 | Sasabe et al. |
| 6,797,735 B2 | 9/2004 | Nagasuna et al. |
| 6,800,666 B2 | 10/2004 | Hahnle et al. |
| 6,822,010 B2 | 11/2004 | Fujimaru et al. |
| 6,828,354 B2 | 12/2004 | Hahnle et al. |
| 6,846,439 B2 | 1/2005 | Kadonaga et al. |
| 6,890,963 B2 | 5/2005 | Clear et al. |
| 6,899,890 B2 | 5/2005 | Kirschner et al. |
| 7,001,548 B2 | 2/2006 | Sakamoto et al. |
| 7,053,131 B2 | 5/2006 | Ko et al. |
| 7,060,287 B1 | 6/2006 | Hubbard et al. |
| 7,138,436 B2 | 11/2006 | Tan et al. |
| 7,393,878 B2 | 7/2008 | Desmarais et al. |
| 7,432,311 B2 | 10/2008 | Mezzenga et al. |
| 7,820,729 B2 | 10/2010 | Akay et al. |
| 1,010,423 A1 | 5/2011 | Mousa et al. |
| 2007/0191963 A1 | 8/2007 | Winterbottom et al. |
| 2007/0198086 A1 | 8/2007 | Kuroda et al. |
| 2007/0213422 A1 | 9/2007 | Collier et al. |
| 2008/0281003 A1 | 11/2008 | Akay et al. |
| 2009/0215913 A1 | 8/2009 | Thies et al. |
| 2010/0068171 A1 | 3/2010 | Guelcher et al. |
| 2010/0326847 A1 | 12/2010 | Jonschker et al. |

FOREIGN PATENT DOCUMENTS

| | | |
|---|---|---|
| CN | 101322854 A | 12/2008 |
| CN | 101322855 A | 12/2008 |
| CN | 101376038 A | 3/2009 |
| CN | 101507839 A | 8/2009 |
| CN | 101698115 A | 4/2010 |
| CN | 102100925 A | 6/2011 |
| EP | 0060138 A1 | 9/1982 |
| WO | WO-9919003 A1 | 4/1999 |
| WO | WO-0034454 A2 | 6/2000 |
| WO | WO-02090958 A2 | 11/2002 |
| WO | WO-2004004880 A2 | 1/2004 |
| WO | WO-2004005355 A1 | 1/2004 |
| WO | WO-2005004811 A2 | 1/2005 |
| WO | WO-2005047435 A2 | 5/2005 |
| WO | WO-2006053031 A2 | 5/2006 |
| WO | WO-2006055940 A2 | 5/2006 |
| WO | WO-2006118987 A1 | 11/2006 |
| WO | WO-2008019940 A1 | 2/2008 |
| WO | WO-2008149096 A2 | 12/2008 |
| WO | WO-2009026387 A1 | 2/2009 |
| WO | WO-2009033088 A1 | 3/2009 |
| WO | WO-2009066283 A2 | 5/2009 |
| WO | WO-2009068912 A1 | 6/2009 |
| WO | WO-2009073068 A2 | 6/2009 |
| WO | WO-2009095153 A1 | 8/2009 |
| WO | WO-2009150113 A1 | 12/2009 |
| WO | WO-2010100506 A2 | 9/2010 |
| WO | WO-2011065987 A1 | 6/2011 |
| WO | WO-2011075183 A1 | 6/2011 |

OTHER PUBLICATIONS

La Gatta et al (Macromol. Biosci. 2005, 5, 1108-1117).*
Akay, G., et al. "Microcellular polyHIPE polymer supports osteoblast growth and bone formation in vitro," Biomaterials 25 (2004) 3991-4000 copyright 2003.
Barbetta, A. et al., "Scaffolds Based on Bioplymeric Foams," Adanced Functional Materials, vol. 15, No. 1 Jan. 2005, pp. 118-124.
Barbetta, A., et al. "Tailoring the Porosity and Morphology of Gelatin-Methacrylate PolyHIPE Scaffolds for Tissue Engineering Applications," Langmuir, vol. 21, No. 26, 2005 12333-12341.
Binks, B.P., et al., "Influence of Particle Wettability on the Type and Stability of Surfactant-Free Emulsions," Langmuir 2000, vol. 16, No. 23, 8622-8631.
Binks, B.P., et al., "Pickering Emulsions Stabilized by Monodisperse Latex Particles: Effects of Particle Size," Langmuir, vol. 17, No. 15, 2001, 4540-4547.
Binks, B.P., et al., "Inversion of Silica-Stabilized Emulsions Induced by Particle Concentration," Langmuir, vol. 21, No. 8, 2005 pp. 3296-3302.
Binks, Bernard P., et al., "Colloidal Particles at Liquid Interfaces," Chapter 6 entitled Solids-Stablized Emulsions: A Review, Robert J.G. Lopetinsky, et al., 2006, pp. 186-224.
Bokhari, M.A., et al. "Polyhipe Polymer: A Novel Scaffold for In Vitro Bone Tissue Engineering," Advances in Experimental Medicine and Biology, Tissue Engineering, Stem Cells and Gene Therapies, 2003, pp. 247-254.
Bruder, Scott P., et al. "Mesenchymal Stem Cells in Bone Development, Bone Repair, and Skeletal Regeneration Therapy," Journal of Cellular Biochemistry, 56:1994, pp. 283-294.
Burdick, Jason A., et al., "Photoencapsulation of osteoblasts in injectable RGD-modified PEG hydrogels for bone tissue engineering," Biomaterials 23 (2002), pp. 4315-4323.
Busby, Wendy, et al., Emulsion-Derived Foams (PolyHIPEs) Containing Poly(-caprolactone) as Matrixes for Tissue Engineering, Biomacromolecules 2001, vol. 2, No. 1, pp. 154-164.
Cameron, N.R., et al., "Study of the formation of the open-cellular morphology of poly(styrene/divinylbenzene) polyHIPE materials by cryo-SEM," Colloid & Polymer Science, vol. 274, No. 6 (1996), pp. 592-595.
Cameron, Neil R., et al., "Chemical modification of momlithic poly(styene-divinylbenzen) PolyHIPE materials," Journal of Materials Chemistry, 1996 6(5), pp. 719-726.
Cameron, Neil R., et al., "The influence of porogen type on the porosity, surface area and morphology of poly(divinylbenzene) PolyHIPE foams," Journal of Materials Chemistry, 2000, 10, pp. 2466-2471.
Cameron, Neil R., et al., "Synthesis and Characterization of Poly(aryl ether sulfone) PolyHIPE Materials," Macromolecules, vol. 30, No. 19, 1997 pp. 5860-5869.
Carnachan, Ross J., et al., "Tailoring the morphology of emulsion-templated porous polymers," The Royal Society of Chemistry, Soft Matter, vol. 2 (2006) pp. 606-618.
Christenson, Elizabeth M., et al., "Biodegradable Fumarate-Based PolyHIPEs as Tissue Engineering Scaffolds," Biomacromolecules, vol. 8, No. 12. (2007), pp. 3806-3814.
Colver, Patrick J., et al., "Cellular Polymer Monoliths Made via Pickering High Internal Phase Emulsions," Chemistry of Materials, vol. 19, No. 7, (2007), pp. 1537-1539.
David, Dganit, et al., "Porous Polyurethanes Synthesized within High Internal Phase Emulsions," Journal of Polymer Science: Part A: Polymer Chemistry, 2009, pp. 5806-5814.
Gurevitch, Inna, et al., "Polymerized Pickering HIPEs: Effects of Synthesis Parameters on Porous Structure," Journal of Polymer Science: Part A: Polymer Chemistry, vol. 48, (2010), pp. 1516-1525.
Ikem, Vivian O., et al., "High Internal Phase Emulsions Stablized Solely by Functionalized Silica Particles," Angewandte Chemie-International Edition, 2008 47(43), pp. 8401-8403.
Jabbari, Esmaiel, et al., "Synthesis, Material Properties, and Biocompatibility of a Novel Self-Cross-Linkable Poly(caprolactone fumarate) as an Injectable Tissue Engineering Scaffold," Biomacromolecules, vol. 6, No. 5 (2005), pp. 2503-2511.
Kim, Taek Kyoung, et al., "Gas foamed open porous biodegradable polymeric microspheres," Biomaterials 27 (2006), pp. 152-159.
Lepine, O., et al., "Preparation of macrocellular PU-PS interpenetraing networks," Polymer 46 (2005) 9653-9663.
Lumelsky, Yulia, et al., "Biodegradable Porous Polymers through Emulsion Templating," Macromolecules, vol. 42, No. 5, 2009, pp. 1627-1633.
Maeda, Hayata, et al., "Pickering-Type Water-in-Oil-in-Water Multiple Emulsions toward Multihollow Nanocomposite Microspheres," Langmuir 2010, 26(17) pp. 13727-13731.

(56) References Cited

OTHER PUBLICATIONS

Menner, Angelika, et al., "High internal phase emulsion templates solely stabilised by functionalised titania nanoparticles," Chemical Communications, 2007 (41), pp. 4274-4276.

Menner, Angelika, et al., "Particle-Stabilized Surfactant-Free Medium Internal Phase Emulsions as Templates for Porous Nanocomposite Materials: poly-Pickering-Foams," Langmuir, vol. 23, No. 5, 2007, pp. 2398-2403.

Mistry, Amit S., et al. "In vivo bone biocompatibility and degradation of porous fumarate-based polymer/alumoxane nanocomposites for bone tissue engineering," Journal of Biomedical Materials Research Part A, 2010, pp. 451-462.

Mistry, Amit S., et al, "Fabriation and in vitro degradation of porous fumarate-based polymer/alumoxane nanocomposite scaffolds for bone tissue engineering," Journal of Biomedical Materials Research Part A, 2009, pp. 68-79.

Moglia, Robert S., et al.; Injectable PolyHIPEs as High-Porosity Bone Grafts; Biomacromolecules, American Chemical Society Publications, Jun. 27, 2011 (pp. A-H).

Peter, Susan J., et al., "Marrow stromal osteoblast function on a poly(propylene fumarate/β-tricalcium phosphate biodegradable orthopaedic composite," Biomaterials, vol. 21, 2000, pp. 1207-1213.

Peter, Susan J., et al., "Crosslinking characteristics of an injectable poly9propylene fumarate/β-tricalcium phosphate paste and mechanical properties of the crosslinked composite for use as a biodegradable bone cement," Journal of Biomedical Materials Research, 1999, pp. 314-321.

Timmer, Mark D., et al., "Effect of physiological temperature on the mechanical properties and network structure of biodegradable poly(propylene fumarate)-based networks," Journal of Biomaterial Science Polymer Edition, 2003, pp. 369-382.

Umez-Eronini, N.O., et al., "Optimisation of Bladder Stromal Culture on Polyhipe," European Cells and Materials, vol. 4, Suppl. 2, 2002, pp. 77-78.

Vignati, Emanuele, et al., "Pickering Emulsions: Interfacial Tension, Colloidal Layer Morphology, and Trapped-Particle Motion," Langmuir, vol. 19, No. 17, 2003, pp. 6650-6656.

Williams, Joel M., et al., "Spatial Distribution of the Phases in Water-in-Oil Emulsions. Open and Closed Microcellular Foams from Cross-Linked Polystyrene," Langmuir, vol. 4, No. 3, 1988, pp. 656-662.

Williams, Joel M., et al., "Emulsion Stability and Rigid Foams from Styrene or Divinylbenzene Water-in-Oil Emulsions," Langmuir, vol. 6, No. 2, 1990, pp. 437-444.

Williams, Joel M., et al., "High Internal Phase Water-in-Oil Emulsions: Influence of Surfactants and Cosurfactants on Emulsion Stability and Foam Quality," Langmuir, vol. 7, No. 7, 1991, pp. 1370-1377.

Youssef, Carlos, et al., "Preparation of Amazingly Hard polyHIPE material from a Direct Emulsion," Materials Research Society Symposium, 2010, pp. 1-6.

* cited by examiner

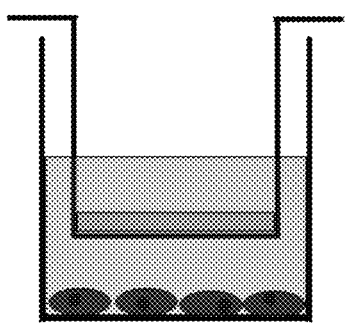
FIG. 10B
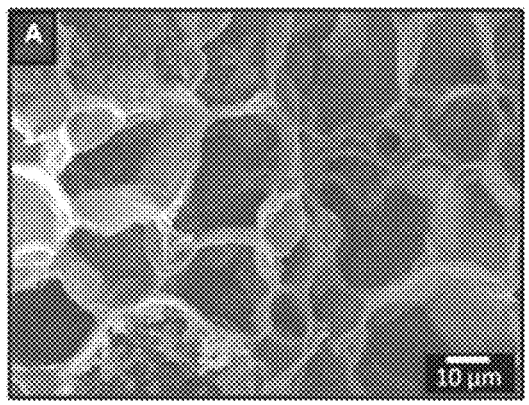 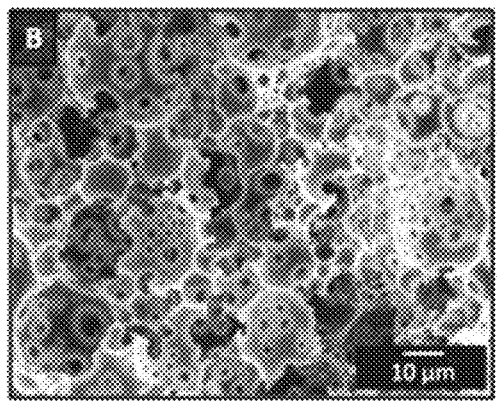
FIG. 11A  FIG. 11B

HIGH POROSITY MATERIALS, SCAFFOLDS, AND METHOD OF MAKING

CROSS-REFERENCE TO RELATED APPLICATION

This application claims the benefit of U.S. Provisional Patent Application No. 61/546,496 filed Oct. 12, 2011. The entirety of the patent application is hereby incorporated by reference to the fullest extent allowable.

STATEMENT REGARDING FEDERALLY SPONSORED RESEARCH OR DEVELOPMENT

The disclosed was made with government support under 1R21AR057531 awarded by the National Institutes of Health and 9826824 awarded by the National Science Foundation. The government has certain right in the invention.

TECHNICAL FIELD

As disclosed herein are high porosity materials and methods of making, said materials are suitable for preparing three-dimensional scaffolds, including scaffolds capable of injection, for encapsulating biologic components, including cells and for use in vivo.

BACKGROUND

Polymerization of high internal phase emulsions (polyHIPEs) generally require either toxic diluents and/or high cure temperatures. The materials as high internal phase emulsions (HIPEs) when formed are generally incapable for use in vivo or in situ.

Use of three-dimensional networks in vivo has been limited by the fabrication and materials used to prepare the three-dimensional network. Many current materials are not injectable. In addition, many current materials do not achieve proper porosity. Furthermore, materials used to prepare three-dimensional networks or scaffolds in vivo have limitations in the compressive strength and modulus of the material when formed as a network or scaffold. It is also found that many materials are not ready for use after fabrication and require additional modifications before use.

SUMMARY

Described herein are injectable polyHIPEs capable of use in vivo. Said polymerization products are well suited for tissue engineering purposes. The product when formed may provide a rigid, high-porosity foam. The product when formed is suitable as a three-dimensional scaffold. The product when formed has sufficient porosity for proper cellular infiltration and/or nutrient waste transport and may be injectable, having, in some embodiments an ability to cure at body temperature. Furthermore, the product when formed offers properties, such as compressive strength and a compressive modulus, that show the product is able to withstand physiological load, such properties being sufficient for stabilization of bone. In addition, the product when formed degrades at a rate that appears to be complementary for tissue regeneration.

Further described herein are methods for making injectable polyHIPEs capable for use in vivo. Said material cures at physiological temperatures. In one form, a process for making the material includes a starting a biodegradable molecule (e.g., macromer) that forms a resulting biodegradable molecule, such as propylene fumarate dimethacrylate (PFDMA). The resulting biodegradable molecule may be synthesized to have an appropriate viscosity and hydrophobicity for emulsification. Synthesis includes use of a surfactant. Surfactant selection includes identification of key structural features of both polymer (e.g., log P values, hydrogen bond acceptor sites) and surfactant (HLB values, hydrogen bond donor sites) that provide one or more stable HIPEs. The process also includes incubation of the one or more HIPEs at about 37° C., which provides, in one form a crosslinking reaction of an unsaturated double bond of certain side groups and continuous phase polymerization for maintaining a desired emulsion geometry.

Still further as described herein are one or more resulting polyHIPE scaffolds that exhibited as much as or greater than 75% porosity, with a pore size range from at least about 4 μm to about 30 μm, and in some forms less than 4 μm and in additional forms greater than 30 μm, including various combinations thereof. In some forms, the scaffold may have an average compressive modulus of at or about 33 MPa and a compressive strength of at or about 5 MPa.

Even further as described herein are one or more resulting polyHIPE scaffolds for use as an injectable, tissue engineered bone graft.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Various embodiments will be explained in more detail with reference to the drawings in which:

FIG. 10B depicts an illustration of the cell viability analysis described with FIG. 10A;

FIG. 11A depicts a representative scanning electron micrograph of pores in a scaffold described herein when prepared with an aqueous phase free radical initiator;

FIG. 11B depicts a representative scanning electron micrograph of pores with interconnectivity in a scaffold described herein when prepared with an organic phase free radical initiator;

DESCRIPTION

Figure 1A:
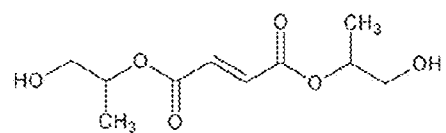
FIG. 1A depicts a representative intermediate molecule as described herein.

Although making and using various embodiments are discussed in detail below, it should be appreciated that as described herein are provided many inventive concepts that may be embodied in a wide variety of contexts. Embodiments discussed herein are merely representative and do not limit the scope of the invention.

Polymerization of high internal phase emulsions (polyHIPEs) is a relatively new method for producing three-dimensional polymer networks also referred to herein as high porosity scaffolds. High internal phase emulsions (HIPEs) are generally characterized by an internal droplet phase volume fraction greater than 74%. Polymerization of the HIPEs in the continuous phase defines an emulsion geometry at a gel point in order to generate a high porosity monolith or polyHIPE. As disclosed herein, a range of porosities (e.g., 75-99%), pore sizes (e.g., 1-100 μm), compressive moduli (e.g., 2 kPa-60 MPa) and morphologies (open pore vs. closed pore) may be produced by varying HIPE composition and processing variables. In addition, as described herein, a polyHIPE system prepared as described will provide a HIPE that retains a viscosity suitable for injection prior to curing.

When providing an injectable polyHIPE system as defined herein, there is: (a) starting molecules and/or macromers that are biodegradable and have suitable viscosities for emulsion formation and (b) reaction thermodynamics that allow polymerization at physiological conditions.

Previous research on developing scaffolds for in vivo use (e.g., for tissue engineering, such as for bone grafts) has focused on styrene-based or unsaturated polyester-based macromers. Although some previous styrene-based systems have excellent pore morphology, they are non-biodegradable. This limits their use as a tissue engineered scaffold. Acrylated esters, while offering limited degradation, include toxic monomers, require a high temperature for curing and are also not injectable. Thus, while some biodegradability was achieved by substituting in unsaturated polyesters, the macromers formed were often too viscous to form HIPEs without the use of a toxic diluent, such as toluene. Many current fumerate-based emulsions, while more biodegradable, require a toxic diluent for HIPE formation and are not injectable.

Described herein are one or more biodegradable and injectable polyHIPE systems. Said polyHIPE systems polymerize in the continuous phase, are capable of locking in at a specified geometry in the emulsion phase, are highly porous (i.e., porosity of about 75 to about 99%), are introduced or injectable into a body portion or tissue prior to curing, are capable of curing in situ after introduction or injection, are capable of forming a highly porous polymeric foam in situ, are biodegradable, and may be modified in terms of porosity and/or one or more mechanical properties in order to offer sufficient mechanical properties to the body portion or tissue into which it is introduced or injected.

Said systems are, in one form, based on starting molecules that polymerize to form a macromer, such as a biodegradable fumerate having ester linkages. The macromer is hydrophobic, allowing for emulsification with water. In addition, the macromer has reactive end groups that crosslinks at lower temperatures. The macromer will exhibit a lower viscosity, replacing (hence not requiring) toxic diluents. In addition, the macromer is typically a product of a two-step reaction, which includes: (a) backbone synthesis, and (b) functionalization.

One example of a suitable macromer is a propylene fumarate dimethacrylate (PFDMA) macromer. The viscosity of the macromer, such as PFDMA, when formed is suitable for HIPE formation and reactive methacrylate end groups enable in situ crosslinking into rigid monoliths in an in vivo environment, such as at body temperature, which is about 37° Centigrade. Fumarate-based polymers may be suitable for tissue engineering, such as serving as a bone graft due to earlier identified osteoconductivity in vivo.

The polyHIPEs are formed herein from starting molecules and when formed may in one or more embodiments exhibit at least about 75% porosity or greater and have pore sizes ranging at least from about 4 μm to at least about 29 μm or greater. The polyHIPEs formed herein also exhibit an average compressive modulus of about 33 MPa and strength of about 5 MPa. The ability to synthesize a fully biodegradable polyHIPE without a toxic diluent that can also cure at physiological temperatures is an important adaptation of emulsion templating that is further described herein. The improved polyHIPEs described herein have various applications, such providing as an injectable form. Said injectable forms may be useful for tissue engineer purposes, such as grafting to bone and other structural purposes.

Figure 1B:
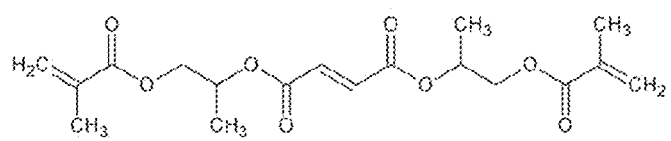
FIG. 1B depicts a representative resulting molecule as described herein.
Figure 2:
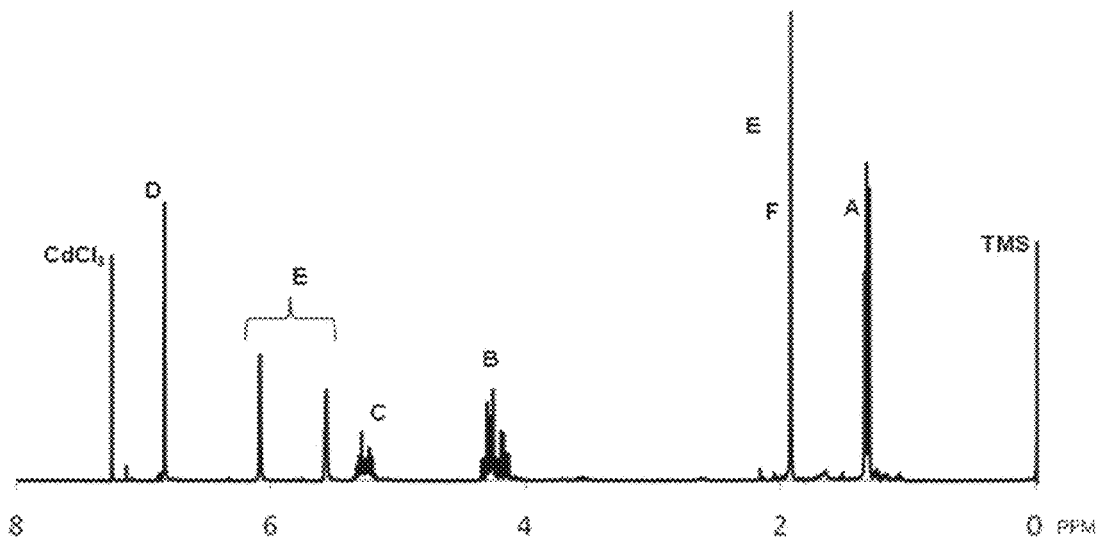
FIG. 2 shows a representative nuclear magnetic resonance (NMR) spectrum of the resulting molecule of FIG. 1B.

Further described is a method of preparing a polyHIPE. In one form the polyHIPE is prepared with a biodegradable fumerate having ester linkages. One example is PFDMA. The method further comprises a two-step process. The first step produced an intermediate molecule as a diester intermediate. In one form the intermediate was bis-(1,2-hydroxypropyl)

fumarate (FIG. 1A). The intermediate was then functionalized with methacrylate endgroups (FIG. 1B). With purification, the structure of the resulting formed material, PFDMA, was confirmed with $^1$H NMR, as represented in FIG. 2. Integration ratio of methacryloyl protons to fumarate protons in the $^1$H NMR spectra was confirmed and the formed structure was, in this example, a PFDMA as a single fumarate unit with two terminal methacrylate groups. The average functionalization was calculated to be greater than 80%. In some embodiments, functionalization was calculated to be at or about 83%. The methacrylate and fumarate groups provided sites for radical crosslinking as further described below. It is, in part, the crosslinking as described herein that allows cure of the HIPE at physiological temperatures. In addition, a resulting macromer described herein from PFDMA had a sufficiently low viscosity (e.g., at or about 125 cP) and hydrophobicity to permit HIPE formation.

In one representative example a suitable macromer, such as PFDMA, was prepared by adding propylene oxide dropwise to a solution of fumaric acid and pyridine in 2-butanone (2.75:1.0:0.033 mol). The reaction was refluxed at about 80° C. until the fumaric acid completely reacted (for approximately 19 hours). Residual propylene oxide and 2-butanone were removed in two distillations steps followed by a redissolving in dichloromethane. The solution was then washed in 0.2 M NaOH/brine (6:4 v/v) until basic to remove residual acidic by-products, was washed with brine, and stirred over anhydrous sodium sulfate to remove residual water. Dichloromethane was removed using rotary evaporation to yield an intermediate molecule, namely a diester bis (1,2 hydroxypropyl) fumarate, as a colorless liquid. The diester was end-capped with methacrylate groups in an addition process with triethylamine and methacryloyl chloride. Hydroquinone was added to inhibit crosslinking during the synthesis. The molar ratios of the diester, methacryloyl chloride, triethylamine, and hydroquinone were 1:2.1:2.1:0.016, respectively. The reaction was maintained below about −10° C. to reduce undesirable side reactions and stirred vigorously overnight under a nitrogen blanket. The macromer was filtered to remove triethylamine salt and neutralized overnight in 2 M potassium carbonate. The solution was washed in 0.1 M NaOH/brine (6:4 v/v) to remove residual byproducts, washed with brine, and stirred over anhydrous sodium sulfate to remove residual water. The dichloromethane was removed by rotary evaporation and a PFDMA structure was confirmed using 1H NMR (300 MHz, CdCl$_3$) with a representative reading of: δ 1.33 (dd, 3H, CH3), 1.92 (s, 3H, CH3), 4.20 (m, 2H, —CH2-), 5.30 (m, 1H, —CH—), 5.58 (s, 1H, —C=CH2), 6.10 (s, 1H, —C=CH2), 6.84 (m, 2H, —CH=CH—). In one form, a final material when formed was a low viscosity liquid with a pale yellow to amber appearance.

Model predictions of the octanol-water partition coefficients (log P) were used as a means of comparing molecular hydrophobicity. Log P values are a measure of the differential solubility of a compound between two immiscible solvents, typically water and a hydrophobic solvent such as octanol. Log P values generally range from negative to positive where a negative value corresponds to a hydrophilic molecule and a positive value a hydrophobic one. The log P value of each compound was calculated from the sum of its non-overlapping molecular fragments. The group contributions were obtained by fitting calculated log P with experimental log P for a training set of more than twelve thousand molecules. The log P value of PFDMA (3.4) was comparable to macromers that have previously formed stable HIPEs as shown in TABLE 1. The octanol-water diffusion coefficient in Table 1 was calculated with the Molinspiration mi Log P model based on molecular structures.

TABLE 1

| Estimated octanol-water partition coefficients | |
|---|---|
| Molecule | LogP[a] |
| Styrene | 2.8 |
| Divinyl benzene | 3.6 |
| PFDA | 2.3 |
| PFDMA | 3.4 |
| PPF (n = 5) | 2.4 |
| PPF (n = 6) | 3.1 |

For the formation of HIPE as described herein, surfactant choice and concentration play a large role in emulsion stability. Historically, selection of HIPE surfactants has largely been based on trial and error and historical precedence. One method of characterizing surfactants is their hydrophilic-lipophilic balance (HLB) classification. Typically, empirical testing is used to ascertain what HLB values are suitable for each application with an HLB range of 2-6 designated for water-in-oil emulsions. Although there are some potential limitations with the HLB approach, it remains a good method for surfactant selection. As described herein, structural features and predictors that may be used to rationally select surfactants for new HIPE macromers are described.

Initially it was suggested that a relationship between surfactant HLB and organic phase hydrophobicity may exist which could then be used to select appropriate surfactants for the PFDMA HIPE. As such, Log P values were utilized as a comparison between established HIPE macromers/monomers and PFDMA (as shown in Table 1). The most widely studied polyHIPE system is styrene and divinylbenzene with log P values ranging from 2.8-3.6. The surfactant sorbitan monooleate (Span 80 with HLB=4.3) is typically used to stabilize styrene-based HIPEs. Therefore, it was hypothesized that resulting materials described herein, such as PFDMA HIPEs with a log P of 3.4, should also form stable emulsions with Span 80. Surprisingly, Span 80 did not stabilize the formed PFDMA emulsion despite a similarity between log P and HLB values. Additional surfactants and combinations of surfactants with structures similar to Span 80 but a range of HLB values from 1.8-15 were evaluated as shown in Table 2. As shown these additional surfactants also failed to form stable HIPEs with PFDMA. Accordingly, it was found that HLB alone is insufficient as a selection criteria for stable HIPE formation.

TABLE 2

Effect of hydrogen bond donor site location and HLB value on HIPE formation
Hydrogen Bond Donor Site Location

| Surfactant | Polar Head | Hydrophobic Tail | HLB value | HIPE Formed |
|---|---|---|---|---|
| Span 85 | 1 | 0 | 1.8 | no |
| Span 80 | 3 | 0 | 4.3 | no |
| PGPR 4125 | 0 | 3 | 4.7 | yes |
| PEG 600 Dilaurate | 0 | 0 | 11.7 | no |
| Tween 80 | 3 | 0 | 15 | no |

For Table 2, Span 80, PEG 600 dilaurate, Tween 80, and PGPR 4125 were studied to observe their effect on PFDMA HIPE formation. Each surfactant had different hydrophilic-lipophilic balance (HLB) values and different hydrogen bond donor sites. PFDMA, surfactant, and DI water (2, 0.4, 8 g, respectively) were vortexed for 5 minutes. HIPE formation was indicated by full incorporation of water without evidence of phase separation after mixing stopped. Successful HIPEs were typically characterized by an opaque, white appearance with a notable increase in viscosity, something that may be similar to mayonnaise. The compositions that resulted in HIPEs were fabricated full-scale to investigate the effect of surfactant structure on pore architecture.

Figure 3A:
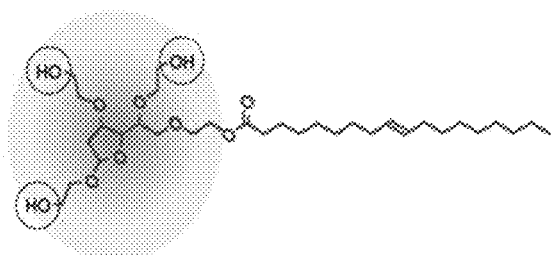
FIG. 3A depicts an less suitable surfactant.
Figure 3B:
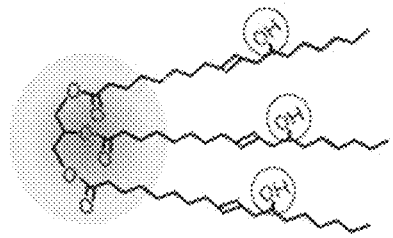
FIG. 3B depicts an more suitable surfactant as described herein.

Surfactant structures were compared to determine differences that might affect PFDMA emulsification. It was found that all of the surfactants tested had hydrogen bond donor sites in the polar head (see FIG. 3A) PFDMA has multiple hydrogen bond acceptor sites in its backbone that could interact with the polar head of the surfactant. It was next hypothesized that this hydrogen bonding prevented the polar head of the surfactant from interacting with the aqueous phase of the emulsion, thereby attenuating its ability to stabilize the organic/water interface.

To avoid using a toxic diluent, a surfactant without hydrogen bond donor sites in the polar head was needed with the appropriate HLB value. The organic soluble emulsifier, polyglycerol polyricinoleate (PGPR) with a comparable HLB (about 4.7) and lack of hydrogen bond donor sites in its polar region, was found to form stable HIPE. Successful formation of PFDMA polyHIPEs with the addition of PGPR indicates that hydrogen bonding does play a role in surfactant stabilization of high internal phase emulsions. Additional surfactants that lack donor sites (e.g., hydrogen bond donor sites) in their polar head may be used to expand the number of biodegradable polymers prepared herein. In addition, given that many biodegradable polymers (e.g. polyesters) have hydrogen bond acceptor sites in their backbone, this may be a preferred route for preparation of other HIPEs.

Figure 3C:
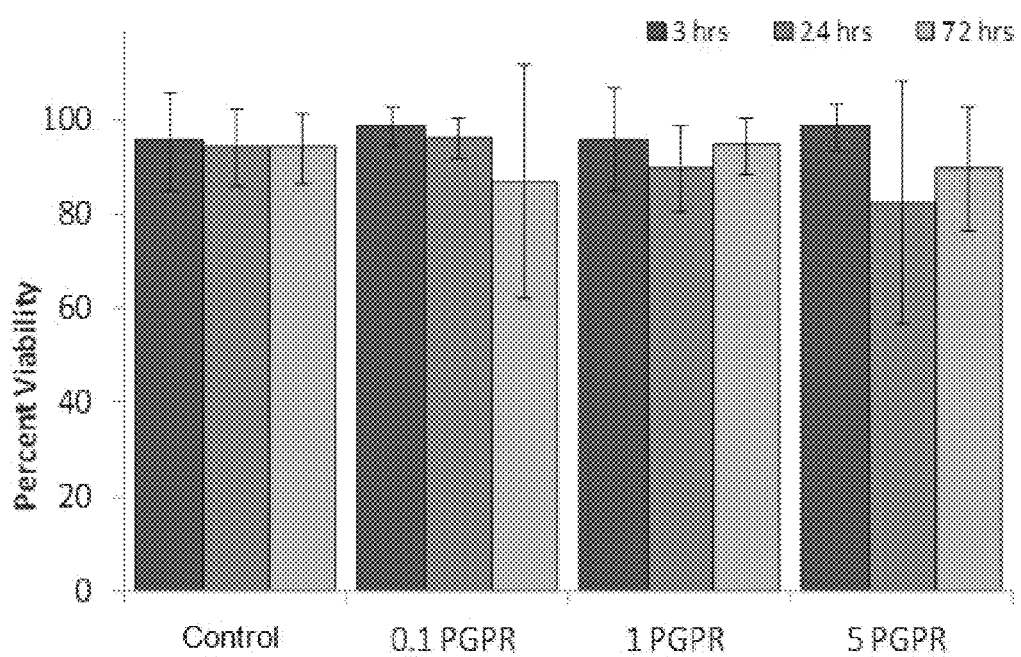
FIG. 3C depicts cytocompability of cells after addition of the surfactant, PGPR, at 0.1 wt. %, 1.0 wt. % or 5 wt. %.

FIG. 3C shows that the stabilizer, PGPR, a surfactant that lacks hydrogen bond donor sites in the polar head, is cytocompatible with cells at concentrations that permit emulsification, which ensures that cells remain viable in the presence of the stabilizer.

PolyHIPE emulsions are prepared as described. In one or more embodiments, a speedmixer, such as a dual asymmetric centrifugal mixer (an example of which is a FlackTek Speedmixer DAC 10 FVZ-K), was used. The macromer, such as PFDMA was mixed with a stabilizer (e.g., the emulsifier or surfactant, such as PGPR) in the speedmixer cup prior to HIPE emulsification. Suitable PGPR concentrations are shown in Table 3. To form the HIPE with the stabilizer lacking hydrogen bond donor sites in the polar head, additional constituents are added, which will include an initiator that facilitates crosslinking and may also assist in stabilizing the emulsion geometry. The initiator may be an aqueous or a nonaqueous free-radical initiator as described further below. The initiator is a suitable crosslinker that initiates radical crosslinking of the macromer chain. The high internal phase emulsion is prepared by mixing and may set at a physiologic temperature of less than 40° C. or about 37° C. for up to or about 24 hours for crosslinking and formation of the three-dimensional network.

Thus, once the macromer with the described emulsifier or surfactant is thoroughly mixed, additional constituents may be added, typically in an aqueous phase. Constituents, in addition, to the initiator (and water, when in an aqueous phase) include at least one or more of an electrolyte. The electrolyte may be a salt and is for preventing Ostwald ripening. In addition, further constituents may also be included that modify the three-dimensional architecture, surface characteristics, as well as mechanical properties of the final product when formed. These constituents include physiologic components, such as media, serum and cells, as well as bioactive modifiers that may or may not include a physiologic or biologic component. Said bioactive modifiers are typically small (about 5-200 nanometers) and often include a hydrophobic component or moiety. An example of a bioactive modifier includes but is not limited to an inorganic nanoparticle. The inorganic nanoparticle may also be linked to a hydrophobic component or fatty acid. Another example of a bioactive modifier includes but is not limited to an amphiphilic molecule having a cell-adhesion moiety (e.g., fatty acid conjugated to cell-adhesion molecule, peptide or protein).

Most if not all of the constituents are typically in an aqueous solution or aqueous droplet phase. An organic phase soluble free radical initiator may also be included or may replace the aqueous phase initiator. In one or more embodiments, the aqueous solution included calcium chloride (1% v/v), ammonium persulfate (5 wt %) and deionized water. Said components were added to the organic phase (PFDMA with 20 wt. % PGPR) in the speedmixer cup. Thus, calcium chloride was the electrolyte for preventing Ostwald ripening and ammonium persulfate was the crosslinker that initiated radical crosslinking of the macromer chains. After mixing, an emulsion was formed, which was transferred to a 37° C. aluminum bead bath for 12 hours to facilitate cross-linking. The resulting polyHIPE was a foam after curing. The foam was a rigid and porous monolith within two hours of curing at 37° C. To remove excess water, the resulting polyHIPE was placed under vacuum (e.g., for about 24 hours) prior to characterization. Characterization showed the representative PFDMA polyHIPE to include closed pores, many of which were, on average, approximately 1 micrometer in diameter, with a porosity of about 74%.

Accordingly, as described herein, stable polyHIPEs of PFDMA were incubated at a physiologic temperature (less than 40° C.) to stabilize the emulsion and initiate radical crosslinking of the unsaturated double bond of the methacrylate groups. The resulting stabilized polyHIPE monoliths when formed were rigid, porous monoliths, often achieved in as early as two hours after curing at the physiologic temperature. The monoliths exhibited at least about 75% porosity and an average compressive modulus of 33 MPa and strength of 5 MPa.

PolyHIPE porosity was measured gravimetrically. Briefly, dried HIPE samples were cut into cubic sections (e.g., 9×9×3 mm) and weighed.

$$\text{Porosity} = 1 - \frac{\rho_H}{\rho_P} \tag{1}$$

Following Equation 1, the HIPE porosity was calculated by comparing HIPE density ($\rho_H$) with the bulk polymer's density ($\rho_P$). Values in Table 3 were an average of nine sections per polyHIPE composition.

TABLE 3

Effect of surfactant concentration on polyHIPE architecture

| Surfactant (wt. %) | Porosity (%) | Average pore diameter (μm) |
|---|---|---|
| 5 | 75.1 ± 0.4 | 29 ± 19 |
| 10 | 75.1 ± 0.3 | 21 ± 11 |
| 15 | 75.1 ± 0.1 | 14 ± 8 |
| 20 | 74.1 ± 0.1 | 4 ± 2 |

Figure 4A:
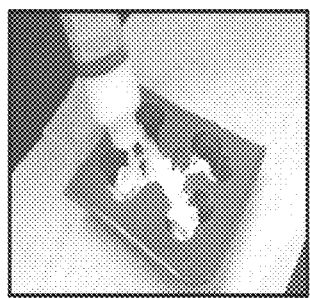
FIG. 4A-4C depict a representative process flow as further described herein.
Figure 4B:
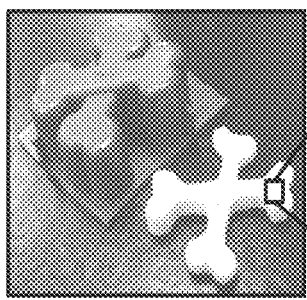
Figure 4C:
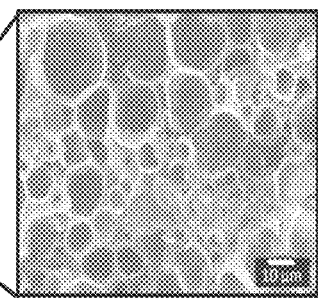

SEM analysis was utilized to determine pore size and morphology of a polyHIPE. Polymerization of the continuous phase of the HIPE locked in the emulsion geometry resulted in a high-porosity foam with a closed-pore morphology and average pore size ranging from at least about 4 to at least about 29 μm (FIGS. 4A-4C) The polyHIPEs described herein, prepared with a biodegradable and osteoconductive polymer, display a pre-cure viscosity suitable for injection (FIG. 4A). In addition, polyHIPEs described herein cure at physiological temperatures, the cured form being a rigid, high-porosity monolith (FIG. 4B, 4C).

It is known that damage to surrounding tissues after deployment of certain polymerizable materials, such as cements, has been attributed to a high polymerization exotherm reaction. Therefore, the reaction exotherm of a three-dimensional material formed as described herein was monitored for 4 hours using a thermocouple inserted into the HIPE as it cured at 37° C. It was found that the temperature of the HIPE did not exceed 37.3° C., which indicates that the mild reaction would not negatively impact surrounding tissues. The cure time of a representative polyHIPE system describe herein (5 wt. % PGPR, 75:25) was quantified at 37° C. by monitoring storage and loss modulus in dynamic mechanical analysis. The described HIPE was found to have a working time of up to or greater than 1 hour (onset of storage modulus increase). In some forms, the described HIPE was fully set within 2 hours (slope of storage modulus→0). It is believed that reactivity of the unsaturated double bond of certain reactive side groups of the macromer and the concentration of an initiator in the polymerization reaction may be modified to modulate these times as desired.

For SEM sampling, circular specimens were sectioned into quarters, fractured at the center of the quarter, sputter-coated with gold, and imaged using FE-SEM (JEOL JSM-7500F). Images at 250× were used to determine the average pore size when the pores were 25-100 μm. Higher magnification (500×, 1000×) images were utilized to determine the average pore size when the pores were less than 25 μm. Each section was imaged in a rastor pattern yielding five images. Measurements were made on at least the first 10 pores along the image median to minimize user bias. Averages pore sizes for each polyHIPE composition are shown (n=150). A statistical correction was calculated to account for non-perfect spherical pores, $h^2=R^2-r^2$, where R is the void diameter's equatorial value, r is the diameter value measured from the micrograph, and h is the distance from the center. The average diameter values were multiplied by this correction factor resulting in a more accurate description of pore diameter. These values are listed in Table 3.

Figure 5A:
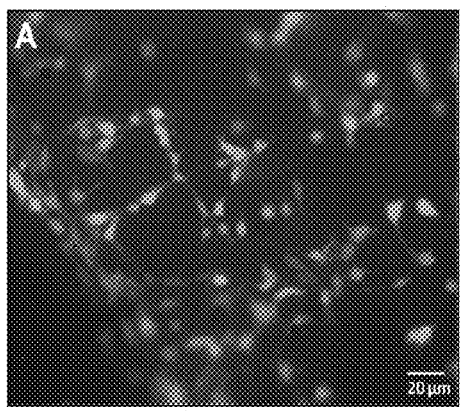
FIG. 5A depicts a representative fluorescent in vitro image of a resulting material described herein.
Figure 5B:
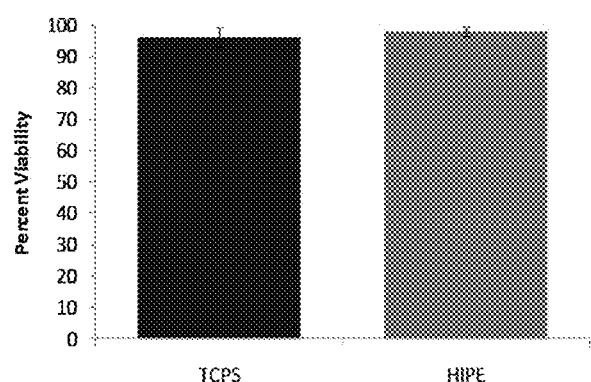
FIG. 5B depicts a representative in vitro comparison of a resulting material described herein as compared with a different material, polystyrene.
Figures 6A, 6B, 6C, 6D:
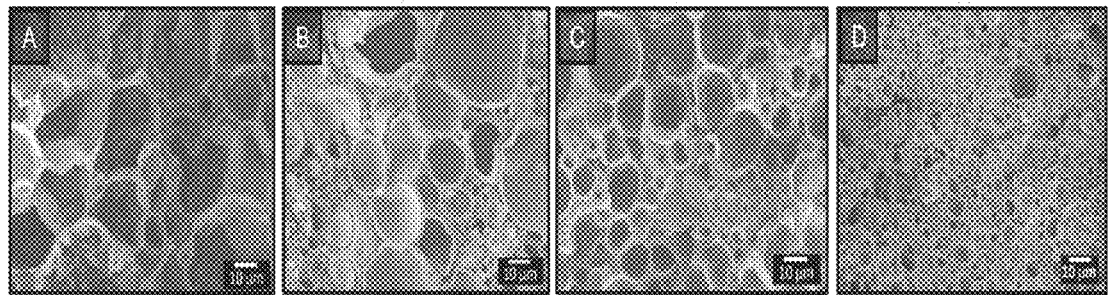
FIG. 6A-6D depict representative scanning electron micrograph (SEM) images of resulting molecules when formed with differing conditions as described herein.

Cytocompatibility analysis of specimens made with 5 wt % PGPR are shown in FIG. 5A and FIG. 5B. In representative in vitro examples with 3T3 fibroblasts, there was a 95% viability of 3T3 fibroblasts after 24 hours. No significant difference was observed between the materials described herein as compared with the same analysis performed with polystyrene for the same duration: polystyrene (96±3%) as compared with a scaffold of HIPE (95±6%). As such, a three-dimensional scaffold formed with a polyHIPE described herein is cytocompatible.

For cell viability a live/dead viability/cytotoxicity kit was used (from Molecular Probes). NIH/3T3 Swiss mouse fibroblast (ATCC-CCL92) were cultured in vitro with a suitable media (including Dulbecco's Modified Eagle Medium (DMEM), Glutamax, high glucose supplemented with 10% heat-inactivated fetal bovine serum (FBS) and 1% penicillin-strepotomycin solution). A polyHIPE sample comprised of 5 wt % PGPR, 75/25 volume fraction, was mixed at 500 rpm. PolyHIPE foams were prepared for cell seeding as follows: UV irradiation (1 hour per side), ethanol wetting ladder and progressive solvent extraction, and overnight media incubation supplemented with 40 v/v % FBS in DMEM. Following overnight incubation in 37° C. and 5% $CO_2$, the culture media was removed and specimens were dried in the hood for 30 minutes, washed 1× with PBS and pre-conditioned with growth medium for 15 minutes. Cells were seeded into wells at 10,000 cells/cm$^2$. Live/dead staining was conducted at 24 hours. Images of each of three specimens were obtained through rastor patterning (n=15) using a fluorescence microscope (Nikon Eclipse TE2000-S). A Student's t-test was performed to determine any statistically significant differences between compositions. All tests were carried out at a 95% confidence interval (P<0.05).

For mechanical testing, formed materials in the form of a polyHIPE foams were mechanically tested with an Instron 3300, equipped with a 1000-N load cell. Generally, three specimens were taken from each sample. The data was then averaged from three sections for each sample tested (n=9). The test specimens were cut into flat rectangular shapes (9×9×3 mm) and compressed at 50 μm/s. Calculations were generally in accordance with ASTM method D1621-04a to determine the compressive modulus. A straight edge and computer software were used to determine the linear region of the stress-strain curve by extending a line from the steepest slope of the curve to the zero-load axis. The point at which this line crossed the axis was determined to be where strain equaled zero and all data points were shifted accordingly. The elastic modulus was equal to the slope of the line in the linear region, as outlined in ASTM D1621-04a. On average, the compressive modulus was about 33 MPa and the strength was about 5 MPa Because polyHIPE architecture is generally dictated by the emulsion geometry prior to cure, modulation of emulsion stability may be used to tune the resulting polyHIPE architecture. This requires a brief review of the thermodynamics involved in both emulsion formation and phase separation. The increase in surface energy of an emulsion compared to the non-emulsified components (ΔW) is a product of both the interfacial energy (σ) and the change in surface area (ΔA) upon emulsification.

$$\Delta W = \sigma \cdot \Delta A \quad (2)$$

ΔW is the free energy of the interface and corresponds to the reversible work brought into the system during emulsification. The magnitude of ΔW can be considered a measure of the thermodynamic instability of the emulsion and drives phase separation as a means to decrease ΔA. From this relationship, it is evident that ultimate stability against coalescence processes is only achieved if σ approaches zero. The surfactant's role during emulsification is to reduce this interfacial tension and form a barrier between the two phases.

At least two relationships relevant to polyHIPE architecture are thus: (1) an increase in interfacial tension (↑σ) will increase the rate of droplet coalescence due to an increase in ΔW; and (2) an increase in interfacial tension (↑σ) will correspond to larger initial droplet sizes (↓ΔA) for a given ΔW. It follows that the surfactant which directly impacts interfacial tension can be used to tune pore sizes by changing the initial droplet size and/or the rate of droplet coalescence prior to cure. It was previously reported that a reduction in surfactant concentration could be used to increase pore size by destabilizing the HIPE. In addition, an increase in surfactant concentration was found to decrease wall thickness and induce pore opening upon polymerization.

As described herein, it is now suggested that HIPE stability may be modulated by changing the surfactant concentration to achieve a range of polyHIPE pore sizes and an open-pore morphology. Representative PGPR concentrations (from 5 to 40 wt %) were evaluated for the effect of surfactant concentration on polyHIPE pore architecture. SEM analysis of polyHIPE monoliths was conducted to quantify pore and interconnect size using the 10.7 pixels/µm ratio at 1000× (see Table 3). Decreasing the concentration of PGPR from, for example, 20 to 5 wt. % increased average pore diameter in PFDMA polyHIPEs (6 to 29 µm) as shown in FIG. 6A-6D. The data and images show pore sizes decreased as PGPR concentration increased from 5-20 wt. %.

Figure 7A:
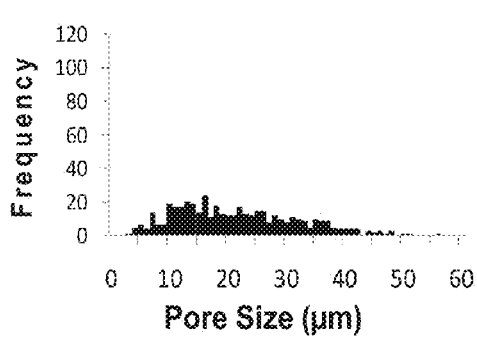
FIG. 7A-7C depict representative pore size distributions graphically displayed for various representative resulting molecules described herein.
Figure 7B:
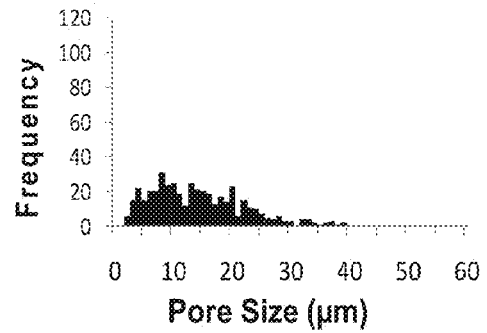
Figure 7C:
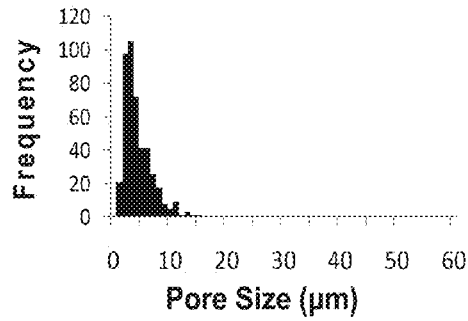

FIGS. 7A-7C show a narrowing of pore size distribution with increasing surfactant concentration. 75/25 polyHIPEs with varied PGPR concentrations were mixed at 500 rpm. The concentration of surfactant was 10 wt. % for FIG. 7A, 15 wt. % for FIG. 7B and 20 w.t % for FIG. 7C. Pore sizes became more uniform as PGPR content increased. The decreased pore size observed at higher surfactant concentration was attributed to a decrease in interfacial tension with a corollary decrease in droplet size, as discussed above. Assuming conservation of organic phase volume, this increase in surface area also decreases the film thickness between droplets; however, wall thinning was insufficient to lead to pore opening in this system.

Based on the above, it is also suggested that increased densification in combination with decreasing film thickness may generate open-pore polyHIPEs.

A narrowing of the pore size histograms also indicated that a higher surfactant concentration resulted in a more uniform pore size (FIGS. 7A-7C). Others have suggested that there is increased pore size homogeneity with increased surfactant due to a reduction in droplet coalescence. However, the droplet coalescence observed and described herein was characterized by a few large pores surrounded by many smaller pores. As illustrated in FIGS. 7A-7C, there was a continuum of pore sizes observed rather than the more bimodal distribution as reported by others. Ostwald ripening has also been reported to increase the pore size distribution of polyHIPEs. In this, diffusion of water from smaller droplets to larger droplets causes a more gradual broadening of the pore size distribution. Both of these processes are affected by the nature and concentration of surfactant; however, it is unclear whether droplet coalescence or Ostwald ripening is responsible for the observed difference in pore size distribution. Based on the histograms alone, it appears that Ostwald ripening may be more significant.

Processing parameters such as mixing speed can also be utilized to tune the pore architecture through manipulation of the emulsion geometry prior to cure. Specifically, it is suggested herein that pore size will decrease and homogeneity increase with an increase in mixing speeds.

Mixing speeds of 500, 1000, and 2000 rpm on a speedmixer were used to evaluate an effect on pore architecture. HIPEs with 10 or 20 wt % PGPR are shown in Table 4. HIPEs with 20 wt % PGPR resulted in minimal change in pore size with an increase in mixing speed.

TABLE 4

Effect of mixing speed on polyHIPE pore structure with a constant volume fraction (75/25) and varied surfactant concentration (10 and 20 wt % PGPR)

| [PGPR] | Mixing Speed (rpm) | Average Pore Diameter (µm) |
|---|---|---|
| 10 wt % | 500 | 21 ± 11 |
|  | 1000 | 8 ± 4 |
|  | 2000 | 4 ± 3 |
| 20 wt % | 500 | 4 ± 2 |
|  | 1000 | 3 ± 2 |
|  | 2000 | 2 ± 1 |

Figure 8A:
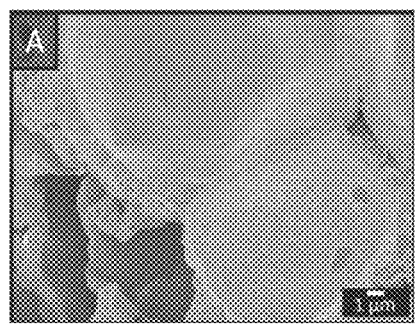
FIGS. 8A-8F depict still further representative SEM images of resulting molecules when formed with differing conditions as described herein.
Figure 8B:
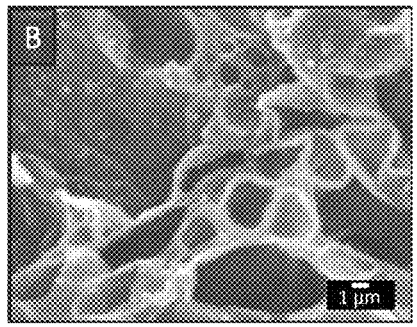
Figure 8C:
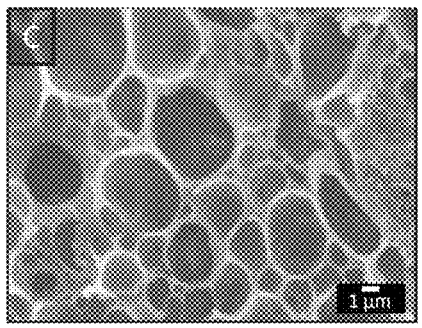
Figure 8D:
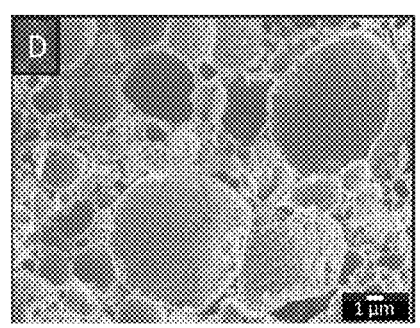
Figure 8E:
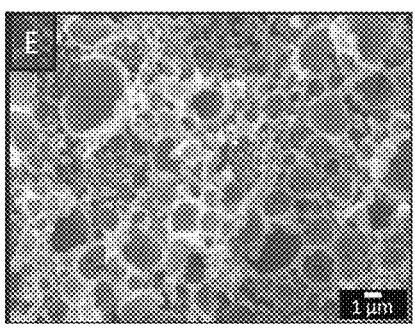
Figure 8F:
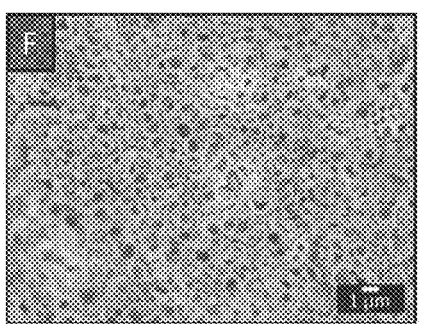
Figure 9A:
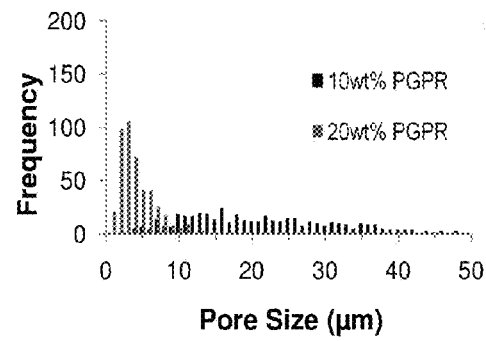
FIGS. 9A-9C depict additional representative pore size distributions graphically displayed for various representative resulting molecules described herein.
Figure 9B:
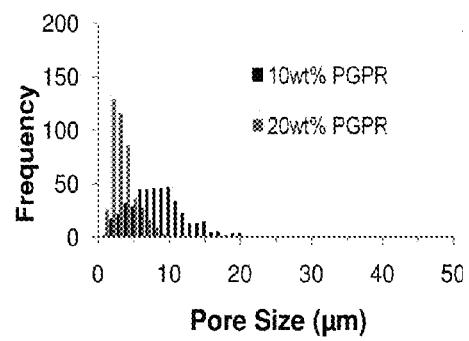
Figure 9C:
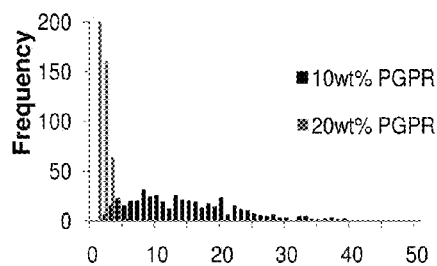

As described herein, it is suggested that destabilizing the emulsion with a lower concentration of PGPR results in a larger pore size distribution, thereby clearly illustrating the effect of mixing speed. Scanning electron micrographs of both 10 wt % PGPR (FIGS. 8A-8C) and 20 wt % PGPR compositions (FIGS. 8D-8F) were mixed at varying mixing speeds. A decrease in pore size was observed with both 10 and 20 wt % PGPR specimens as mixing speed was increased (500 to 2000 rpm). The trend was more evident with the 10 wt % PGPR specimens and further illustrates the effect of surfactant on emulsion stability and pore architecture. A narrowing of the histograms in FIGS. 9A-9C from 500 to 2000 rpm, respectively, indicated a more homogeneous pore size distribution, which was illustrated in the SEM images. As stated previously, increased surfactant produced an increase in pore homogeneity due to decreased surface energy. Combining both mixing speed and surfactant had a large effect on pore size homogeneity as indicated by a more narrow distribution in FIG. 9A-9C.

Figure 10A:
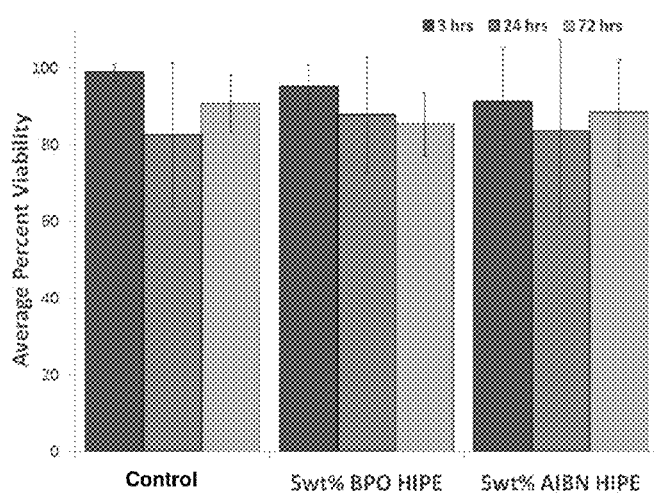
FIG. 10A depicts a representative chart showing cell viability at 3 hours, 24 hours and 72 hours after seeding on media containing a scaffold prepared as described herein, which included an organic phase free radical initiator of either benzoyl peroxide (BPO) or azobis-isobutyronitrile (AIBN)

The three-dimensional architecture of the polyHIPE emulsion, and hence, final formed network when cured may also be modified by use of alternative initiators. In one example, organic-phase soluble initiators (e.g., organic soluble free radical initiators) were found to alter pore shape and provide a three-dimensional interconnectivity within the scaffold. Said initiators are typically those with decomposition temperature ranging from between about 25 to about 100° C. Examples include but are not limited to azobis-isobutyronitrile (AIBN) and benzoyl peroxide (BPO). Preliminary tack-free time studies of polyHIPE emulsions prepared with 5 wt. % AIBN or BPO indicated a longer cure time compared with emulsions prepared with 5 wt. % ammonium persulfate. The time to cure was about 7-12 hours with an ammonium persulfate initiator (aqueous phase free radical initiator) as compared with about 1.5 hours with the AIBN or BPO (organic soluble free radical initiator). The organic soluble free radical initiators do not appear to leach components from the scaffold that effect cell growth and viability, as depicted in FIG. 10A, in which human mesenchymal stem cells were seeded on the base of wells and samples of scaffolds described herein were introduced into the medium, as depicted in FIG. 10B. Neither 5 wt. % AIBN or 5 wt. % BPO appeared to greatly effect cell viability after 72 hours.

Figure 12A:
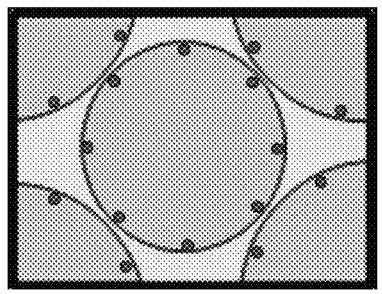
FIGS. 12A-12C further illustrate a proposed sequence for pore formation when a scaffold described herein is prepared with an aqueous phase free radical initiator.
Figure 12D:
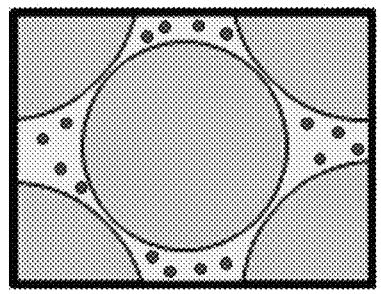
FIGS. 12D-12F further illustrate a proposed sequence for interconnectivity when a scaffold described herein is prepared with an organic phase free radical initiator.
Figure 12B:
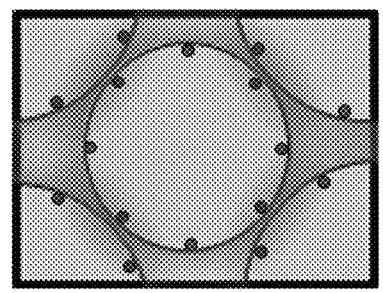
Figure 12E:
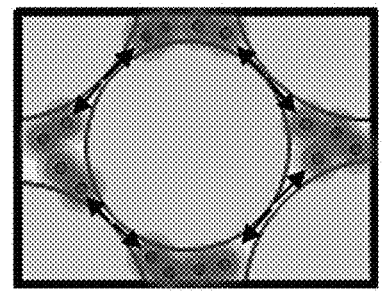
Figure 12C:
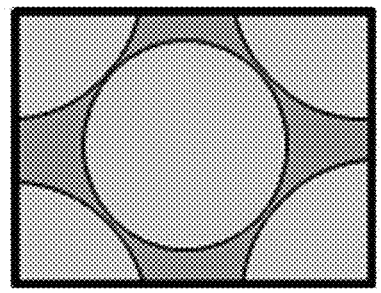
Figure 12F:
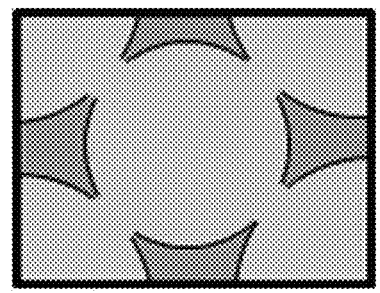

FIG. 11B depicts a representative alteration in pore interconnectivity with addition of an organic-phase soluble initiator (BPO) as compared with an alternative aqueous free radical initiator (ammonium persulfate) also used and described herein (FIG. 11A). With the organic-phase soluble initiator, initiation is believed to begin within the organic phase, in the initiator (circles) appears to alter the direction of densification forces (arrows) of the macromers (straight and bent lines) (FIG.), which create interconnected pores. FIGS. 12A-C show a proposed mechanism for pore formation with use of an aqueous phase free radical initiator as described herein, in which initiation is believed to originate from the aqueous phase at the pore wall. With organic soluble free-radical initiators there is a tearing of the pore wall for interconnect formation, which is due to forces generated during macromer densification (FIGS. 12D-12F). As the macromers crosslink and form a network, the addition of chains creates a force that pulls on the polymer film surrounding the water droplets. The densification forces pull at the polymer film, thinning the film and increasing the ability for rupture, forming the interconnections. This is contrasted with the method proposed for aqueous phase free-radical initiators (FIGS. 12A-12C), in which initiation from the aqueous phase at the pore wall provides densification forces that appear to counteract in a manner that stops or prevents tearing of the polymer film. On the other hand, in our system initiated in the organic phase.

For three-dimensional scaffolds described herein, the behavior of the surfactant may be further modified to improve cell adhesion to the scaffold of cells, such as fibroblasts, mesenchymal stem cells, osteoblasts, chondrocytes, and other matrix formed cells. For example, PGPR was found to effect cell adhesion to the scaffold. PolyHIPEs were prepared with PGPR and initiated with AIBN. When cured, as previously described, samples were sectioned using a precision diamond wafering saw. Prior to seeding with human mesenchymal stem cells (hMSCs), the polyHIPEs samples were soaked in 70% ethanol to sterilize, subjected to a wetting ladder to increase aqueous solution penetration, and incubated overnight in medium enhanced with 40 wt. % fetal bovine serum (FBS). The scaffolds were then seeded at a concentration of about $2 \times 10^3$ and $10 \times 10^3$ cells/cm$^2$. On scaffolds fabricated with PGPR, hMSC adhesion and spreading declined when measured between 3 and 24 hours after seeding. It was hypothesized that PGPR may be affecting protein adsorption and/or their conformation when attempting to localize on the polyHIPE scaffold. This was further analyzed on PFDMA films prepared with and without PGPR. The effect of PGPR on protein adsorption and/or conformation was confirmed at 24 hours, in which hMSC adhesion and spreading decreased on PGPR-PFDMA film specimens as compared with control (PFDMA alone) specimens. This suggested that a cell-binding sequence may facilitate adsorption of cells to the polyHIPE network. Further it was believed that the pore wall of the formed scaffolds could be altered to facilitate cell adhesion to the scaffolds. Thus, functionalizing PGPR and/or introducing fatty acids with HLB values (e.g., steric acid, oleic acid) compatible with or recognized by cells (e.g., the cell binding motif, such as RGD) as described herein will further enhance cell adhesion to the described scaffolds.

PolyHIPEs described herein were fabricated without toxic solvents or monomers at cure temperatures appropriate for in situ deployment. These improved polyHIPEs are porous and may be suitable as an injectable for tissue engineering purposes, such as a tissue graft. The effect of surfactant structure on HIPE stability as described herein further provides a useful method for selective preparing any number of desired polyHIPE compositions. In addition, the mixing conditions described herein allow for a wide selection of polyHIPE formulations, particularly for tissue engineering applications.

Figure 13A:
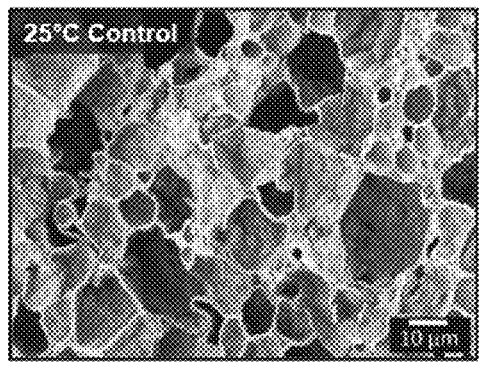
FIGS. 13A and 13B depict representative scanning electron micrographs of a scaffold described herein before (13A) and after (13B) cold storage for 48 hours at −20° C.
Figure 13B:
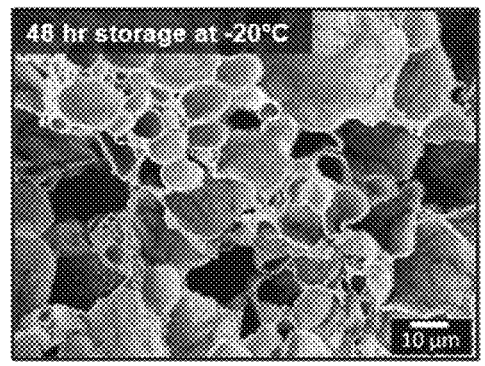

The capability of the material as described herein to be injectable prior to curing and for in situ curing and formation of a scaffold has also been described. The viscosity was controlled by choice of and/or quantity of surfactant and/or initiator. As such, defects in a body tissue, such as bone or cartilage, may be filled with a material described herein prior to curing, without flowing out of the site. The described material may be frozen and later thawed for use. In one or more embodiments, an emulsion described herein may be prepared prior to curing to have a consistency that can be described as similar to mayonnaise, which may be frozen and subsequently thawed for direct injection or introduction in a body site in need. Thus, a material described herein is both injectable prior to curing and may be prepared (in a non fully cured state) in advance, eliminating unnecessary mixing and preparation just prior to injection. In addition, a scaffold described herein may also be prepared, cured to form its three-dimensional structure, and stored for a period of time prior to use. FIGS. 13A and 13B are scanning electron micrographs representing a pre-cured PFDMA polyHIPE shortly after curing (FIG. 13A) and after thawing from storage for 48 hours at −20° C. (FIG. 13B). The illustrations show that there appears to be no effect on polyHIPE stability and pore architecture after cold storage.

Figure 14A:
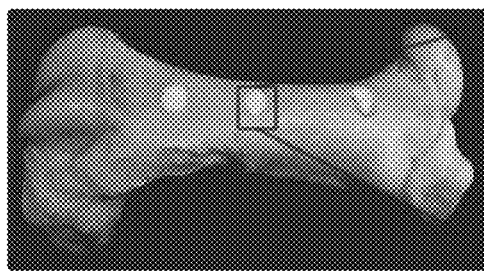
FIG. 14A depicts a bone after introducing in an injectable form prior to curing a material described herein in which the material has cured after injection.
Figure 14B:
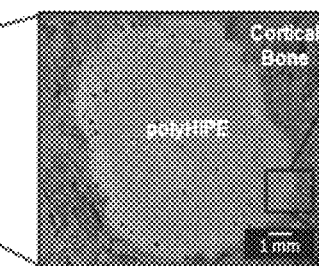
FIG. 14B depicts a magnification of the boxed section in FIG. 14A.
Figure 14C:
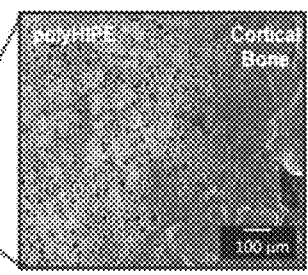
FIG. 14C, depicts a magnification of the boxed section in FIG. 14B.

An example of a PFDMA polyHIPE that was injected (prior to curing) and integrated and cured in host tissue in vitro without forming any gap between the tissue and the scaffold is illustrated in FIGS. 14A-C. FIG. 14A shows the injectable PFDMA polyHIPE successfully filled the irregular defect in situ in bone. The scanning electron micrographs in FIGS. 14B and 14C illustrate the gap-free interface between the bone and the cured polyHIPE. The illustrations further show the space-filling ability of the material when cured in situ and its ability to fully infiltration a site of interest.

By providing a variance of formulations, materials and scaffolds formed therefrom as described herein may serve as a tissue graft for new tissue formation, growth and remodeling. The material selection may be designed to meet the tissue requirements. For example, a polyHIPE of PFDMA should promote, among other things, stem cell infiltration and/or tissue integration (e.g., osteointegration, chondrocytic integration) and be suitable as a graft for tissue such as bone or cartilage. Such a material for seeding of living cells will offer fewer complications than current alloplastic materials, including stainless steel, titanium, methylmethacrylate resins, polyethylene, silicone elastomers, and hydroxyapatite ceramics, by providing tissue integration, biodegradability, and stress shielding.

As described herein, bioactive substances or modifiers may also be introduced to the emulsion prior to curing. Said substances or modifiers have, in the past, been difficult because the introduction of many substances, such as nanoparticles, alter phase hydrophobicities and change polyHIPE emulsion stability. It has been found, however, that a bioactive compound that includes nanoparticles ranging in size from 5 to 200 nanometers and is modified with fatty acids or compounds that introduce hydrophobicity may be introduced to a material prior to curing as further described herein. Examples include inorganic nanoparticles, such as hydroxyapatite nanoparticles or an amphiphilic molecule with a cell-adhesion moiety or fatty acids conjugated to cell-adhesive peptides or proteins m. Said modified bioactive substances because of their size and hydrophobicity will self-assemble at the oil-water interface of an emulsion when prepared as describe herein.

A representative modifier is one that may promote repair of the tissue into which the scaffold described herein is introduced to. Taking advantage of a modifier that may offer a longer lifespan to the material (e.g., inorganic component rather than organic component), hydroxyapatite nanoparticles were introduced in an injectable form of a PFDMA polyHIPE. The effect of non-coated hydroxyapatite nanoparticles on HIPE stability was investigated by observing phase separation before gel point relative to a non-stabilized HIPE control. It was found that hydroxyapatite nanoparticles alone destabilized the emulsion as indicated by larger droplets.

Figure 15:
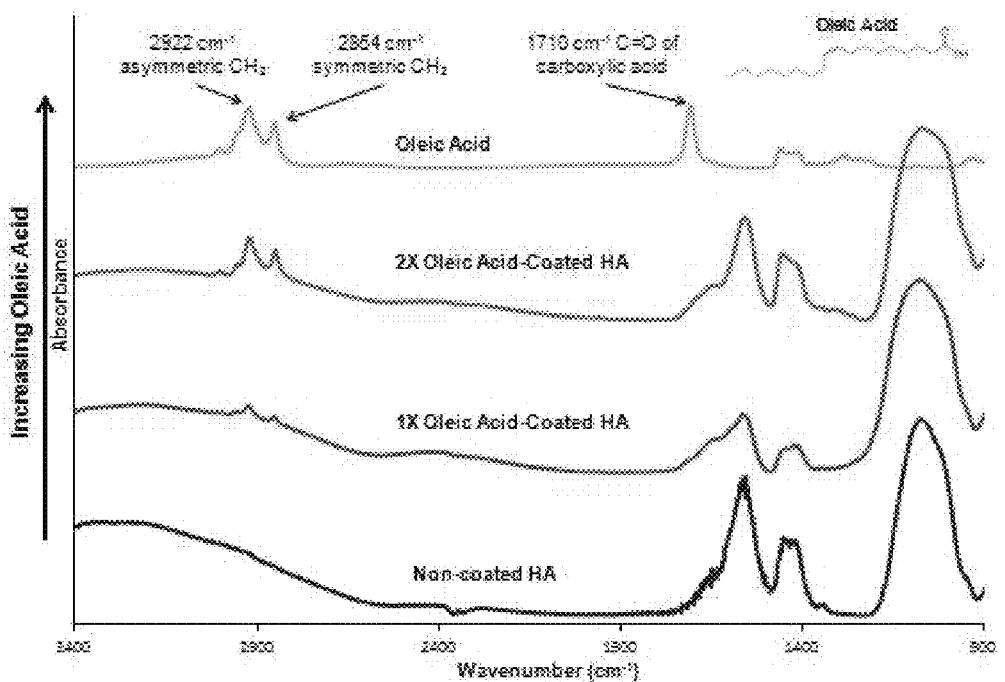
FIG. 15 depicts relative amounts of fatty acid adsorbed as described herein to a surface of hydroxyapatite nanoparticles.

With this understanding, particle hydrophobicity was altered by adsorbing surfactant to hydrophilic hydroxyapatite particles. An oleic acid coating procedure was adapted to coat hydroxyapatite nanoparticles with various concentrations of oleic acid; relative amounts were confirmed with FTIR as depicted in FIG. 15. Nanoparticles transition from soluble to insoluble in water after oleic acid coating. Hence, polyHIPE emulsions were prepared and stabilized with 10 wt % PGPR and containing 1-4 wt. % non-oleic acid coated hydroxyapatite nanoparticles. When cured, the scaffold exhibited an increase in pore size with the addition of nanoparticles. This was believed to indicate a decrease in HIPE stability.

A scaffold prepared as described herein offers a three-dimensional architecture and an interconnected porous structure for promoting cellular ingrowth and proliferation, vascularization, and the transport of nutrients and metabolic waste. In addition, the scaffold described herein offers an opportunity to encapsulate and/or deliver cells to a specific site, such as a site of injury. The described scaffold overcomes the inability of other proposed delivery systems (e.g., hydrogels) that cannot withstand the physiologic load necessary for promoting cell growth, particular in certain tissue such as bone and cartilage. As such, described herein is a method of encapsulating cells and stabilizing cells in the material after curing, in which the material when formed and cured exhibits mechanical integrity and can be also delivered in situ to a particular body location.

Figure 16:
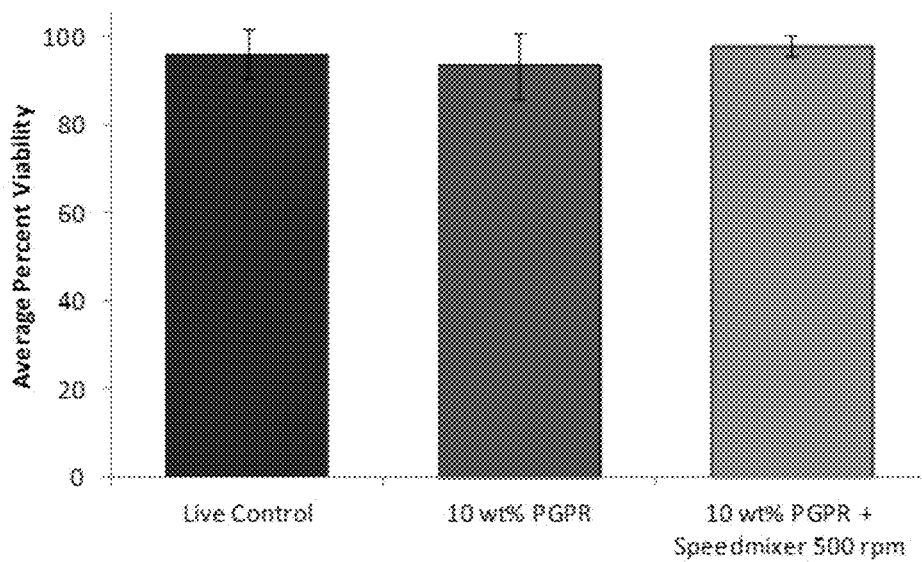
FIG. 16 depicts a representative chart showing cell viability of cells alone as compared with cells in an emulsion described herein.

Cells were initially prepared in an emulsion to determine cell viability after mixing at the necessary emulsion speed. FIG. 16 shows that cells were viable after 24 hours both in PFDMA polyHIPE with 10% PGPR and when the same PFDMA polyHIPE with 10% PGPR was subjected to a mixing speed of 500 rpm after 24 hours. The cells appear viable in the emulsion. For longer durations, cell viability is enhanced with addition of a simplified media or a growth-promoting medium (with or without serum).

Figure 17A:
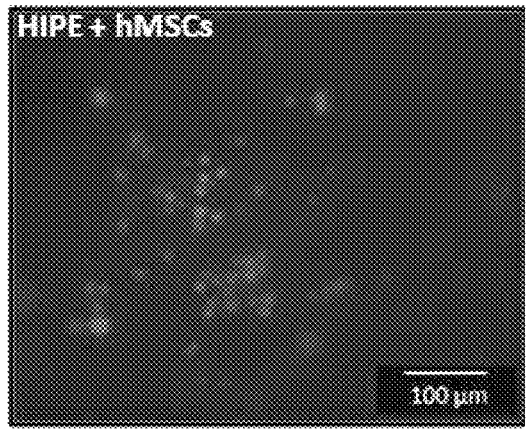
FIG. 17A depict localization of cells remaining viable (17A) in a scaffold described herein after encapsulation therein as compared with a control scaffold that did not encapsulate cells (FIG. 17B)
Figure 17B:
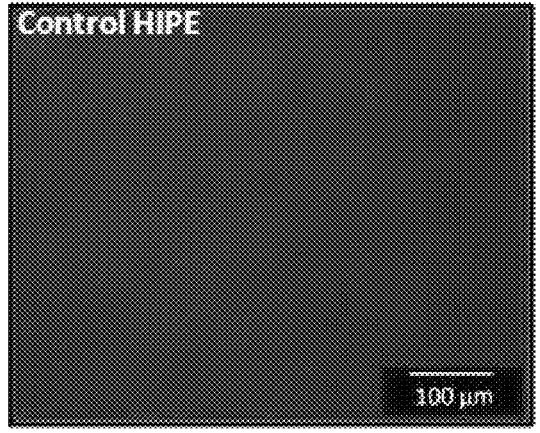
Figure 18A:
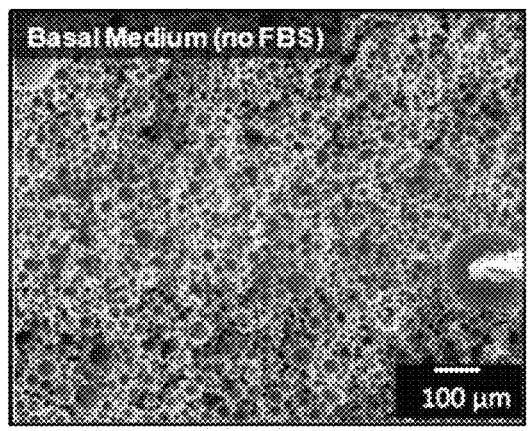
FIGS. 18A and 18B illustrate pore size and architecture of a scaffold described herein with a basal media (18A) and with a complete media that included 16.5 wt. % fetal bovine serum (18B).
Figure 18B:
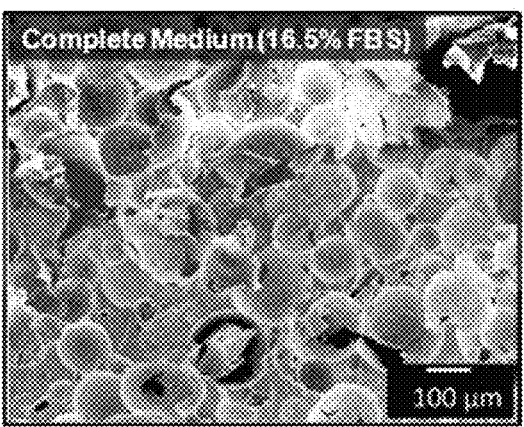

After confirming viability of a cell with a emulsion described herein, hMSCs were successfully encapsulated in a cured PFDMA polyHIPE scaffold. Approximately, 1.5 million cells stained with an fluorescent die (CellTracker™ Orange) were incorporated into the aqueous phase comprised of media supplemented with 16.5% fetal bovine serum and 1% calcium chloride and mixed with the organic phase having 5 wt. % AIBN in the a speedmixer, as previously described. The polyHIPE emulsion with encapsulated cells was cured overnight in a 37° C. incubator with 5% $CO_2$ in a beaker filled with aluminum beads to increase heat conduction. Following cure, a foam was formed and cells therein were fixed with a 3.7% glutaraldehyde solution for six hours, sectioned, and imaged utilizing fluorescent microscopy. The presence of encapsulated cells is illustrated in FIG. 17A. It was observed that addition of fetal bovine serum in the aqueous phase may have decreased HIPE stability, as indicated by an increase in voids and overall pore size in the pore architecture. This is depicted in FIG. 14B, which is with 16.5% fetal bovine serum, as compared with FIG. 14A, which is with supplementation with a basal media without serum. The data should be reproducible and, furthermore, shows also that the architecture of the emulsion as well as the formed scaffold may be readily modified as desired. A larger pore size may, for example, enhance degradation as well as cell migration and/or infiltration.

Thus, the composition of constituents added to the emulsion, both to the aqueous and the non-aqueous allow the finally formed material (foamed monolith) to exhibit a unique and desired property. Importantly, the formed scaffold exhibits sufficient mechanical strength and modulus to withstand physiological loading in order to restore tissue function without causing deleterious stress-shielding effects. By design, the described scaffold by introducing it in situ may match a number of irregular geometries of certain tissue or tissue defects while promoting cell integration and tissue healing. Injectable grafts of a suitable porosity that retains high mechanical strength and is capable of curing in situ as described herein are preferable to other scaffolds, including those that are more costly and/or time-consuming (generated by computer-aided design molds) and require post-fabrication modifications.

While the invention has been illustrated and described in detail in the drawings and foregoing description, such illustration and description are considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The foregoing description is of examples embodying, at least in part, certain teachings of the invention. The invention, as defined by the appended claims, is not limited to the described embodiments. Alterations and modifications to the disclosed embodiments may be made without departing from the invention. The meaning of the terms used in this specification are, unless expressly stated otherwise, intended to have ordinary and customary meaning and are not intended to be limited to the details of the illustrated structures or the disclosed embodiments. Although the foregoing description of embodiments have shown, described and pointed out certain novel features of the invention, it will be understood that various omissions, substitutions, and changes in the form of the detail as illustrated as well as the uses thereof, may be made by those skilled in the art, without departing from the scope of the invention. Particularly, it will be appreciated that the one or more embodiments may manifest itself in other configurations as appropriate for the end use of the material made thereby.

What is claimed is:

1. A high internal phase emulsion composition comprising:
   a biodegradable macromer obtained from a two-step reaction comprising backbone formation and functionalization forming reactive end groups for crosslinking the biodegradable macromer at a temperature below 40 degrees Centigrade, the biodegradable macromer provided as a blend without a toxic diluent and with a surfactant lacking polar head group hydrogen bond donor sites;
   an electrolyte to prevent Ostwald ripening;
   a free radical initiator for crosslinking; and
   water,
   the high internal phase emulsion polymerizable at the temperature below 40 degrees Centigrade.

2. The high internal phase emulsion of claim 1, wherein the high internal phase emulsion includes the electrolyte, the free radical initiator, and the water in an aqueous phase is.

3. The high internal phase emulsion of claim 1, wherein the backbone of the biodegradable macromer comprises hydrogen bond acceptor sites.

4. The high internal phase emulsion of claim 1, wherein the two-step reaction includes backbone formation of a diester intermediate and functionalization forming reactive end groups comprising methacrylate end groups.

5. The high internal phase emulsion of claim 1, wherein the biodegradable macromer is propylene fumarate dimethacrylate.

6. The high internal phase emulsion of claim 1, wherein the biodegradable macromer is an ester-based hydrophobic macromer having ester linkages.

7. The high internal phase emulsion of claim 1, wherein the surfactant is organic phase soluble having a hydrophilic-lipophilic balance value in a range of 2 to 6 while lacking the polar head group hydrogen bond donor sites to stabilize the biodegradable macromer having ester linkages.

8. A tissue compatible scaffold composition made from a high internal phase emulsion comprising:
    a blend of a macromer of propylene fumarate dimethacrylate emulsified without a toxic diluent and with a surfactant lacking polar head group hydrogen bond donor sites; and
    water in an aqueous phase,
    the macromer having an average functionalization greater than 80% and crosslinked at a temperature below 40 degrees Centigrade.

9. The tissue compatible scaffold composition of claim 8, wherein the scaffold composition further comprises a free radical initiator and is injectable at the temperature.

10. The tissue compatible scaffold composition of claim 8, wherein the scaffold composition does not fully cure for about two hours.

11. The tissue compatible scaffold composition of claim 8, wherein the scaffold composition when cured has a porosity of at or greater than 75%.

12. The tissue compatible scaffold of composition claim 8, wherein the scaffold composition when cured had an average pore diameter of at least 4 to 29 micrometers.

13. The tissue compatible scaffold composition of claim 8, wherein the scaffold composition when cured has an average compressive modulus of at or about 33 mPa.

14. The tissue compatible scaffold composition of claim 8, wherein the scaffold composition when cured has an average strength of at or about 5 mPa.

15. A method of making a high internal phase emulsion comprising:
    combining a starting biodegradable hydrophobic macromer capable of forming a high internal phase emulsion with a surfactant that lacks polar head group hydrogen bond donor sites to form a blend without a toxic diluent, the macromer comprising a backbone having ester linkages and hydrogen bond acceptor sites and is functionalized with reactive end groups that crosslink at a temperature below 40 degrees Centigrade;
    adding in droplets an electrolyte that prevents Ostwald ripening, a free radical crosslinking initiator and water to the blend; and
    emulsifying to form the higher internal phase emulsion.

16. A method of making a three-dimensional scaffold comprising:
    combining a starting biodegradable hydrophobic macromer capable of forming a high internal phase emulsion with an organic phase soluble surfactant that lacks polar head group hydrogen bond donor sites to form a blend without a toxic diluent, the macromer comprising a backbone having ester linkages and hydrogen bond acceptor sites and is functionalized with reactive end groups that crosslink at a temperature below 40 degrees Centigrade;
    adding in droplets to the blend while mixing an electrolyte that prevents Ostwald ripening, a free radical crosslinking initiator and water;
    emulsifying to form the higher internal phase emulsion;
    allowing the higher internal phase emulsion to set at a physiologic temperature below 40 degrees Centigrade.

17. A high internal phase emulsion comprising:
    a biodegradable hydrophobic macromer emulsified without a toxic diluent and with a surfactant that lacks polar head group hydrogen bond donor sites, the macromer comprising a backbone having ester linkages and hydrogen bond acceptor sites and is functionalized with reactive end groups that crosslink at a temperature below 40 degrees Centigrade;
    an electrolyte to prevent Ostwald ripening;
    a free radical initiator for crosslinking; and
    water,
    the high internal phase emulsion polymerizable at the temperature below 40 degrees Centigrade.

18. The high internal phase emulsion of claim 17, wherein the surfactant is provided in a range from 5 to 20 wt. % and when decreased from 20 to 5 wt. % average pore diameter of the high internal phase emulsion increases.

19. The high internal phase emulsion of claim 17 wherein the surfactant concentration is from 5 to 40 wt. %.

20. The high internal phase emulsion of claim 17 wherein the high internal phase emulsion has a higher average pore diameter when emulsified at a mixing speed greater lower than 1000 rpm.

21. The high internal phase emulsion of claim 17 further comprising one or more bioactive compounds containing at least one hydrophobic moiety promoting interaction with an organic phase in the high internal phase emulsion.

22. The high internal phase emulsion of claim 17 further comprising one or more bioactive compounds.

23. The high internal phase emulsion of claim 17 further comprising a plurality of cells introduced in an aqueous phase of the high internal phase emulsion.

24. A tissue compatible scaffold composition as a high internal phase emulsion containing in an organic phase a polymerizable macromer of propylene fumarate dimethacrylate emulsified without a toxic diluent and with an organic phase surfactant lacking polar head group hydrogen bond donor sites encapsulating a plurality of viable cells in an aqueous phase, the aqueous phase further comprising an electrolyte to prevent Ostwald ripening and a free radical initiator.

* * * * *